United States Patent [19]

Nilson

[11] 4,312,344
[45] * Jan. 26, 1982

[54] SYRINGE

[75] Inventor: Nils B. Nilson, Mjölby, Sweden

[73] Assignee: Kenova AB, Malmo, Sweden

[ * ] Notice: The portion of the term of this patent subsequent to Dec. 2, 1997, has been disclaimed.

[21] Appl. No.: 136,763

[22] Filed: Apr. 3, 1980

[51] Int. Cl.³ .............................................. A61M 5/24
[52] U.S. Cl. ............................. 128/216; 128/218 D; 128/218 P
[58] Field of Search .................. 128/215, 216, 218 R, 128/218 P, 218 PA, 218 D, 234, 207.25; 222/95–107

[56] References Cited

U.S. PATENT DOCUMENTS

| | | | |
|---|---|---|---|
| 2,737,946 | 3/1956 | Hein, Jr. | 128/207.25 |
| 3,135,260 | 6/1964 | Hamilton | 128/218 R |
| 4,008,718 | 2/1977 | Pitesky | 128/234 X |
| 4,236,516 | 12/1980 | Nilson | 128/216 |

Primary Examiner—John D. Yasko
Attorney, Agent, or Firm—Finnegan, Henderson, Farabow, Garrett & Dunner

[57] ABSTRACT

A syringe with a plunger reciprocable therein has a collapsible container removably attached to the discharge end of the barrel. The container can be collapsed by means of the plunger. The stroke volume of the plunger between displaced positions thereof corresponding to the container being empty and filled, respectively, is substantially equal to the volume of the container.

26 Claims, 9 Drawing Figures

SYRINGE

BACKGROUND OF THE INVENTION

1. Field of the Invention

This invention relates to improvements in syringes for effecting subcutaneous, intravenous, intramuscular and rectal injections of medicaments and the like into human beings and animals and for taking blood samples therefrom.

More particularly, the syringe of the invention is of the type in which only a small part of the apparatus is discarded after each use, the rest of the syringe being used repeatedly.

2. Description of the Prior Art

It is well known that most syringes now used in hospitals, offices and health centers are of the disposable type, i.e. are disposed of or discarded after one use. These syringes usually comprise two pieces: a barrel and a plunger mounted for reciprocable movement in the barrel, both parts usually being made of plastic material.

As a disposable product, a syringe of this type, although made by modern mass production methods such as injection moulding, is relatively expensive due to the materials and precision involved in the manufacture thereof.

It has been proposed to combine a barrel and a plunger with a replaceable container positioned at the discharge end of the barrel, the container being introverted or collapsed upon itself in use by action of the plunger to eject or administer the medicament contained in the container. A syringe of this type is diclosed in U.S. patent application Ser. No. 684,020 (Nils Billy Nilson) filed May 7, 1976 (now abandoned).

In the syringe disclosed in said patent application the container forms the end wall of the barrel and comprises a substantially rigid first wall portion at the exterior side of the end wall and a flexible second wall portion at the interior side of the end wall and introvertible upon the inside surface of the first wall portion. A nozzle is provided on said first wall portion for attaching a hypodermic needle thereto.

In the embodiment of this prior art syringe as described in said patent application the container is formed as a spherical bulb having substantially the same diameter as the cylinder space formed by the barrel. When an empty container is attached to the barrel said flexible second wall portion being introverted upon the inside surface of said first wall portion, and the container is to be filled, the piston is withdrawn and the flexible wall portion is carried along by the piston due to subatomospheric pressure created between the piston and the flexible wall portion while liquid such as blood or a medicament is being sucked into the container. However, it has been found that a substantial subatmospheric pressure (vacuum) will be created by the piston during the later part of the displacement thereof, which requires a considerable force to be applied to the piston at the end of the stroke necessary for filling the container. Under circumstances the container cannot even be completely filled. Moreover, the force has to be maintained on the piston; if the piston is released it will spring back and part of the liquid in the container will be expelled. This means that in case of a medicament to be administered the portioning thereof will be inaccurate and insufficient, and that in case of a blood sample to be taken, hazardous reinjection of the blood into the vein will take place.

Said drawback of the prior art syringe also presents itself at the safety step always performed in the administration of a medicament into a human being when the cannula has been put in, to make sure that the cannula is in the proper position for the specific administration to be performed. This safety step commonly called aspiration is performed by first ejecting a minimum quantity of the medicament from the container before the cannula is put in and then, when the cannula has been put in, withdraw the piston slightly. If blood enters the container the cannula has pierced a vein and if not, the cannula is inserted into the tissues. Thus, it can be checked if the cannula is in proper position for an intravenous or an intramuscular or a subcutaneous injection. Due to the vacuum created in the prior art syringe according to said patent application it is difficult to make the said check at the administration even if the container used is a prefilled container.

A problem of the syringe described in said patent application may also be seen in the difficulty of completely emptying the container by actuating the plunger to eject or administer the medicament contained in the container, due to the fact that the container is not completely collapsed when the plunger bottoms therein. This is a serious drawback in many cases wherein the medicament comprises a small volume which has to be administered with great accuracy.

SUMMARY OF THE INVENTION

The primary object of the present invention is to overcome the foregoing problems and disadvantages of the prior art by providing a syringe wherein the stroke volume of the piston is related to the volume of the container in order to eliminate the creation of a substantial subatmospheric pressure when the piston is withdrawn for filling the container.

Another object of the invention is to provide a syringe wherein the plunger can adjust itself to the form of the container in order to completely empty the container.

Additional objects and advantages of the invention in part will be set forth in the description which follows and in part will be obvious from the description or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the syringe of this invention comprises an elongated barrel having a discharge end, a container, means for removably attaching the container to the discharge end of the barrel to form the end wall thereof, said container having a substantially rigid first wall portion at the exterior side of the end wall and forming an inside surface, and a flexible second wall portion at the interior side of the end wall and introvertible upon the inside surface of the first wall portion, a nozzle on said first wall portion for attaching a hypodermic needle thereto, and a plunger reciprocably mounted in the barrel, the stroke volume of the plunger between displaced positions thereof corresponding to the container being empty and filled, respectively, being substantially equal to the volume of the container.

In a preferred embodiment of the syringe of the invention the container is spherical and the barrel forms a cylindrical cylinder space. In that case the cylinder has an inside diameter which is less than the inside diameter of the spherical container. In this embodiment the plunger comprises a stem displaceably guided for axial movement in the barrel, and a resilient plunger head connected to the inner end of the stem, so that the plunger head although the diameter thereof is less than the diameter of the container, can be deformed to engage said flexible second wall portion when introverted upon the inside surface, over the entire surface thereof.

Preferably, the resilient plunger head comprises a hollow plunger head of a resilient material connected to the stem to enclose the inner end thereof, the inner surface of the plunger head being spaced from the inner end surface of the stem.

In a further preferred embodiment the hollow plunger head comprises an annular spherical end wall portion having an outside radius of curvature corresponding substantially to the radius of curvature of said flexible second wall portion of the container, when introverted upon the inside surface of said first wall portion of the container, a central end wall portion spherically domed towards the interior of the hollow plunger head, and a side wall portion joining the annular end wall portion, said side wall portion surrounding the stem spaced therefrom and being attached to the stem at a location spaced from said inner end thereof.

It is also preferred that the hollow plunger head forms a conical lip on the outside thereof flared towards the end of the barrel which is opposite the discharge end thereof, and engaging the inside wall surface of the barrel, said lip allowing air to pass between the plunger and the inside wall surface of the barrel when the plunger is being displaced towards the discharge end, and being forced to sealing engagement with said inside wall surface of the barrel when the plunger is being displaced away from the discharge end of the barrel.

The invention also provides a hollow plunger head to be used in a syringe of this type, comprising a spherically curved annular end wall portion, a central end wall portion domed spherically towards the interior of the hollow plunger head, and a side wall portion joining said annular end wall portion, which tapers slightly towards said central end wall portion.

The accompanying drawings which are incorporated in and constitute part of this specification, illustrate one embodiment of the invention and together with the description serve to explain the principles of the invention.

DESCRIPTION OF THE PREFERRED EMBODIMENTS

Figure 1:
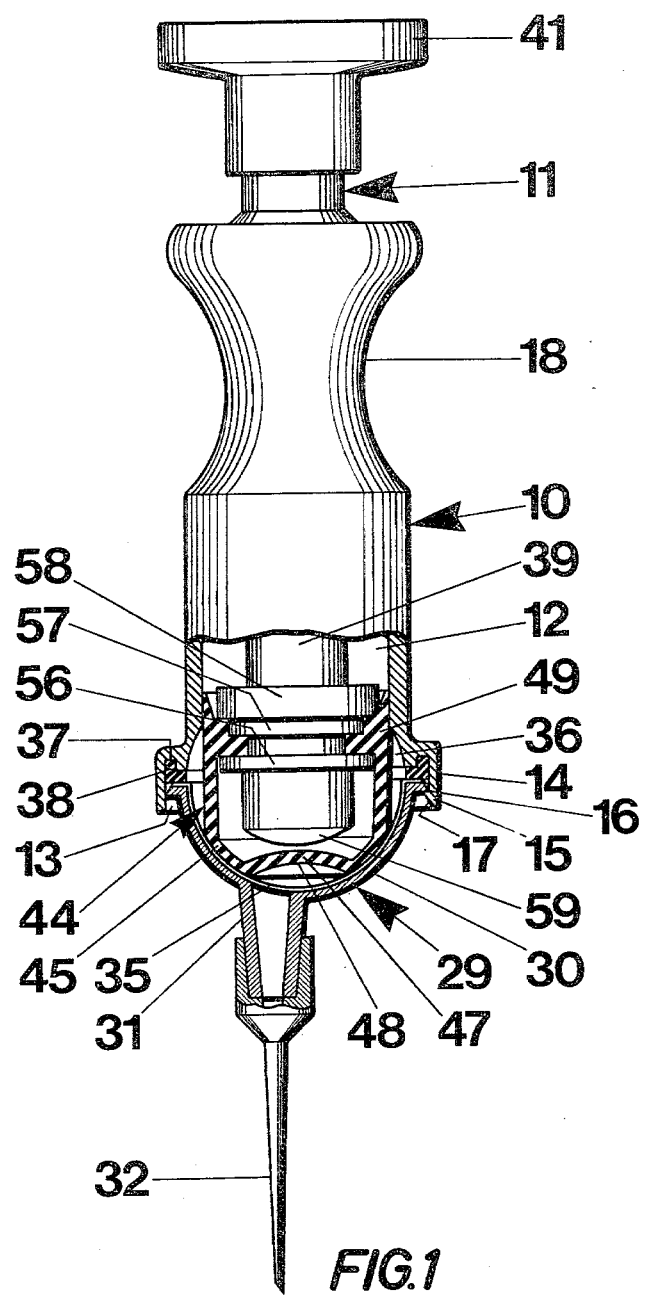
FIG. 1 is a side view partly in axial cross section of the preferred embodiment of the syringe constructed according to the teachings of the invention, shown with an empty container attached to the barrel.

Reference will now be made in detail to the present preferred embodiments of the invention, examples of which are illustrated in the accompanying drawings.

Referring to the drawings, which disclose in detail the construction of the syringe according to the teachings of the invention, such a syringe provides a two-part unit which is constructed for repeated use and comprises an elongated barrel 10 having a discharge end, and a plunger 11 reciprocably mounted in the barrel. This barrel can be made as an integral element entirely of metal or a plastic material and preferably is made of a transparent plastic material.

The barrel forms a cylindrical cavity 12 which widens into an enlarged cylindrical socket 13 at the discharge end of the barrel, said socket being defined at its periphery by an integral wall 14. At the edge of wall 14 there are formed on the inside surface thereof three circumferentially spaced inwardly directed ribs 15 each of which extends over substantially 30°. Each rib forms an inwardly facing shoulder 16 and tapers from said shoulder towards the free edge of wall 14 to form a conical guide surface 17. At the end opposite of the discharge end the barrel has a circumferential recess 18 having a concave or rounded shape, which provides a finger grip at which the barrel may be gripped during the operation of the syringe.

The barrel forms a cylindrical passage 19 extending from the inner end or bottom 20 of cavity 12 through the finger grip portion 18 and opening at the flat end surface 21 of the barrel where the passage forms an enlargement 22, a conical transition 23 being provided between said enlargement and the rest of the passage 19. Enlargement 22 has at the opening thereof a circumferential rounded rib or bead 24. A plug 25 is received by the enlargement 22 and is retained therein against the transition 23 by rib or bead 24 which engages a circumferential flange 26 on the plug, guidingly engaging the inside cylindrical surface of the enlargement 22. Plug 25 forms a cylindrical passage 27 in register with passage 19 and having the same diameter as said passage, and a conical protuberance 28 is formed on the outside end surface of plug 25 around passage 27.

A container or cartridge constructed to be removably attached to the discharge end of the barrel to form the end wall thereof is generally indicated at 29 and comprises a substantially rigid hemispherical first wall portion 30 at the exterior side of the end wall. Said first wall portion forms an externally protruding eccentrical nozzle 31 conically tapered towards the outer end thereof, for attaching a hypodermic needle or cannula 32 thereto.

Means for removably attaching the container to the discharge end of the barrel comprises a circumferential circular flange 33 on the container, which has a bevelled edge 34. Flange 33 can have a V-shaped notch in the lower side thereof or can merge into a conical rim protruding outwardly in the same direction as nozzle 31 on one side of flange 33, as disclosed in detail in the patent application referred to above. Said first wall portion 30 of container 29 preferably is made of a suitable transparent plastic material, such as polypropene or polyester, and can be manufactured by injection moulding. The container further comprises a flexible second wall portion 35 at the interior side of the end wall formed by the container when attached to the barrel. Said second wall portion is connected to the other side of flange 33 preferably by adhesive, melting or ultrasonic welding. Wall portion 35 preferably is made of a suitable flexible transparent plastic material. In a preferred embodiment wall portion 35 is made of a laminate comprising an outside sheet of Nylon or polyester and an inside sheet of polypropene, said sheets being interconnected by an adhesive. A semi-spherical dome forming the inside wall portion 35 of the container is produced of this laminated material in a deep drawing or vacuum-forming operation. It is introvertible upon the inside surface of container wall portion 30 to a collapsed position shown in FIGS. 1, 8, and 9, and in this position container wall portion 35 is seen to be dimensioned and formed so as to contact the concave inside surface of wall portion 30 of the empty container, following the curvature of said wall portion. This is the condition in which the container may be delivered.

Container 29 is connected to barrel 10 by pushing socket 14 onto flange 33 of the container to receive the flange in socket 14. When the barrel is being slid over flange 33 to receive the flange in socket 14, the flange flexes or gives resiliently when sliding against ribs or lips 15 and then, after having slipped over said ribs or lips, springs out by resiliency to engage at the edge thereof the inside shoulder 16 formed by each rib or lip. By the engagement thus obtained between the barrel and the container this will be retained by the barrel as shown in FIGS. 1, 2, 7, and 8.

Figure 2:
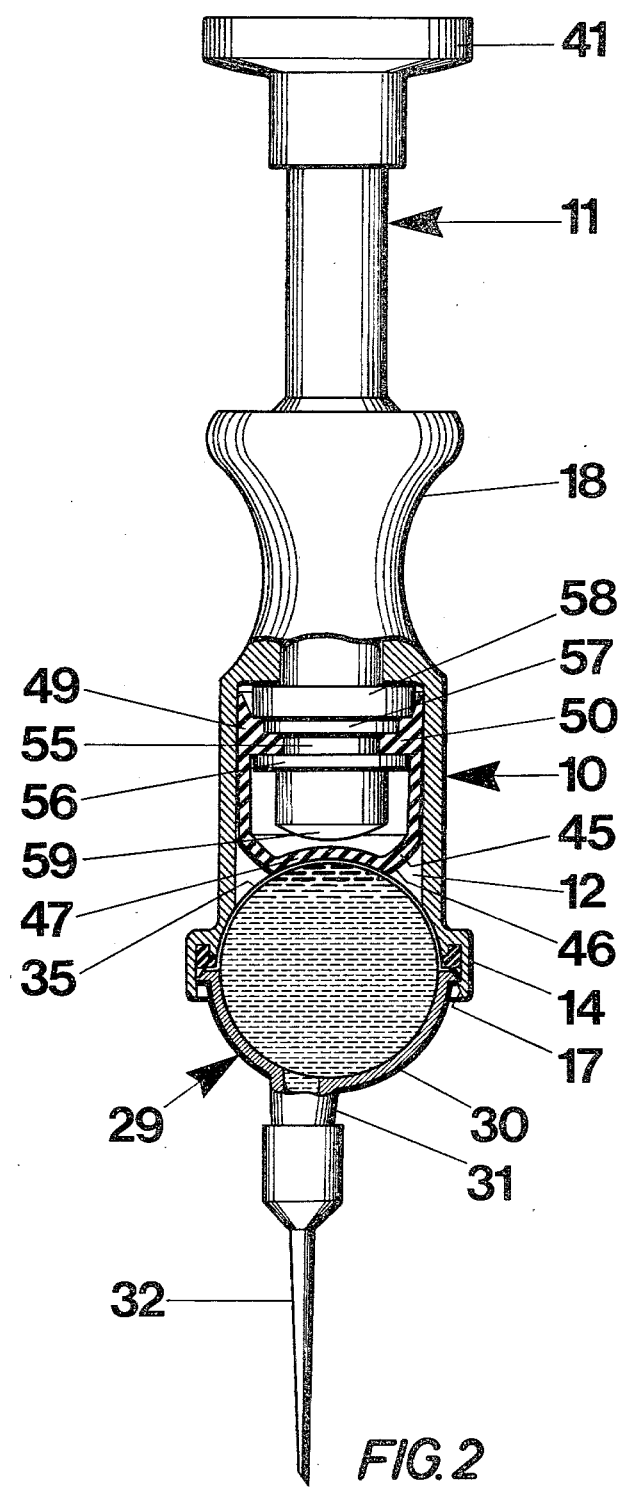
FIG. 2 is a view similar to FIG. 1 of the syringe with the container filled prior to ejection of the liquid contained therein.
Figure 3:
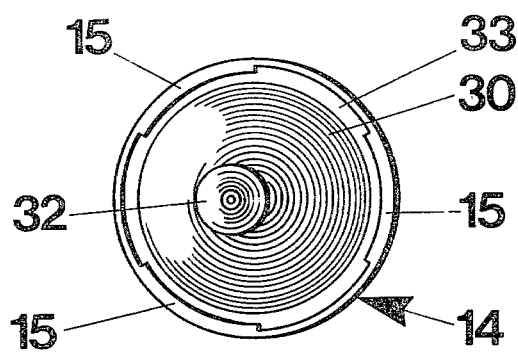
FIG. 3 is an end view of the syringe as seen from the container end thereof.

When container 30 is completely filled with liquid as shown in FIG. 2, it has spherical form, the inside diameter thereof being greater than the inside diameter of the cavity 12 for the purpose of the invention as will be explained in more detail below. Inside the barrel 10 there is provided at the transition thereof into socket 14 an annular enlargement 36 of cavity 12 defined by a spherically curved portion of the inside wall of the barrel, which matches the spherical form of the filled container part of which is received therein as shown in FIG. 2. Moreover, at the transition between the barrel 10 and the socket 14 there is provided a groove 37 receiving a gasket 38 with angular cross-sectional form, which seals the discharge end of the barrel against flange 33 so that cavity 12 is sealed against the surroundings at the discharge end of the barrel when a filled or empty container is attached thereto as described.

Plunger 11 comprises a cylindrical stem 39 which is received in the combined passage 19, 27 and is slidable therein. Clearance 19' and 27' is provided for stem 39 in passage 19 and 27, respectively, to allow air to pass between cavity 12 and the surrounding atmosphere.

Stem 39 forms a threaded outer end 40 and a disc 41 formed with a socket 42 integral therewith and provided with inside threads is screwed onto end 40. Socket 42 has an internally bevelled end surface 43 having the same size and the same angle as the protuberance 28 so that said protuberance can be received in the socket 42 when stem 39 is pushed inwards into the barrel and the end surface 43 engages the protuberance 28.

Figure 4:
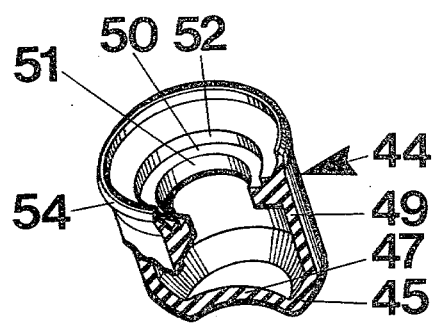
FIG. 4 is a broken perspective view of the hollow plunger head forming part of the syringe.
Figure 5:
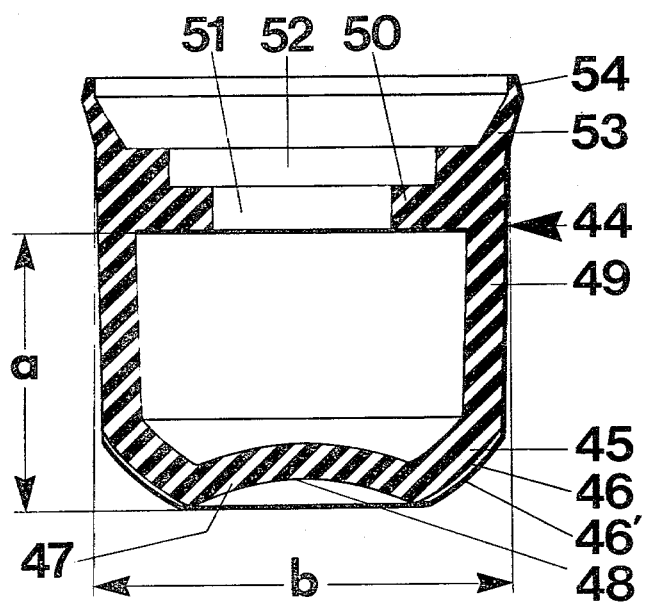
FIG. 5 is an enlarged view in axial cross section of the hollow plunger head.

Stem 39 is provided at the inner end thereof with a hollow plunger head 44 which is made of a resilient rubber or plastic material. With reference more specifically to FIGS. 4 and 5, the plunger head 44 comprises an annular end wall portion 45 which is spherically curved on the outside surface 46 thereof. The annular wall portion 45 surrounds a central end wall portion 47 which has an outside spherically curved concave surface 48. A side wall portion 49 joins the annular wall portion 45 and tapers slightly on the outside thereof towards portion 45. Wall portions 45, 47, and 49 have a unitary wall thickness. At the end opposite to wall portion 45 said side wall portion 49 joins an inwardly directed annular flange 50 defining a circular opening 51 forming a circular countersink 52. A flared portion 53 having conical inside and outside surfaces, projects from flange 50 and terminates in a lip portion 54 which forms a conical outside surface tapering towards the free end of the lip portion.

Stem 39 forms an annular groove 55 between two annular flanges 56 and 57, and the hollow plunger head 44 is mounted to the stem by the flange 50 being received in said groove, flange 56 being located on the inner side of flange 50, and flange 57 being received by countersink 52. Flange 57 is integral with an enlarged flange 58 on stem 39, which is received inside portion 53 of the plunger head. Thus, it will be seen that the inner end of stem 39 is surrounded by side wall portion 49 of the plunger head, and at this end the stem forms a convex end surface 59 which is spherically curved and has substantially the same diameter as the central end wall portion 47 of the hollow plunger head 44, the convex inside surface of portion 47 being located opposite to the convex end surface 59 of the stem spaced therefrom.

When received in cavity 12 of barrel 10 portion 53 of plunger head 44 slidingly engages the inside cylindrical surface of the barrel and is resiliently deformed to exert pressure against said surface. Thus, portion 53 sealingly engages, due to the inherent elasticity thereof, the inside cylindrical surface of cavity 12. Said portion acts as a valve member as will be described later.

In the preferred embodiment of the syringe according to the invention as described herein the radius of curvature of portion 45 of the hollow plunger head 44 is substantially the same as the radius of curvature of the inner side of the flexible wall portion 35 of the container when introverted against the inside surface of wall portion 30 of the container and accurately following the form thereof as shown in FIG. 1. The concave surface 48 of the central portion 47 of the plunger head has substantially the same radius of curvature as the outside surface of wall portion 35 of container 29 when filled completely with liquid as shown in FIG. 2 wherein the filled container has substantially spherical form. The radius of curvature of the convex end surface 59 of stem 39 equals the radius of curvature of container wall portion 35 when following the form of container wall portion 30 in the introverted condition, less the wall thickness of portion 47 of the hollow plunger head 44.

The container can be delivered empty in a sterilized condition, wall portion 35 of the empty container being introverted to contact the concave inside surface of wall portion 30 of the empty container following the curvature of said wall portion as shown in FIG. 1.

In the operation of the syringe the container is attached to the barrel 10 in the manner described and as shown in FIG. 1. If the plunger head 44 is not already contacting the outside surface formed by wall portion 35 collapsed against and following the curvature of the inside surface of wall portion 30, of the empty container it is displaced manually to such position to contact wall portion 35 as is also shown in FIG. 1. When the plunger head is being moved towards the container at the discharge end of the barrel, said end being closed off by the container forming an end of the barrel, air enclosed in front of the moving plunger will pass between the plunger head and the cavity wall due to the valve action of the conical lip 53 of the plunger head as mentioned above. The atmosphere communicates with the interior of the barrel through the clearance 19' and 27' around stem 39 in passages 19 and 27.

Cannula 32 is then inserted in a bottle or the like containing a liquid medicament to be received by the container, or in a blood vessel in order to take a blood sample therefrom, as the case may be. When the plunger 11 is retracted, the conical lip 53 of the plunger head 44, sliding along the inside wall of cavity 12, will sealingly engage said wall due to the fact that it will expand towards that wall by friction between the lip and the wall. The part of the cavity 12 enclosed between the plunger head and the inner end of the cavity is vented through the clearance 19' and 27' formed around stem 39 in passages 19 and 27 so that no pressure builds up behind the plunger head. However, a subatmospheric pressure (partial vacuum) will be created in cavity 12 between the plunger head and the end wall formed at the discharge end of the barrel by container 29, a leak-proof seal being provided between the container and socket 14 by sealing ring 38. No air will be able to pass into this space from the surroundings, since an effective seal will be maintained also between lip 53 and the inside surface of the barrel when the plunger is retracted from the discharge end as explained above. By the subatmospheric pressure thus created wall portion 35 will be progressively withdrawn from wall portion 30 to the position shown in FIG. 2 in which the container has been filled with liquid.

For the purpose of the invention the inside diameter of the cylinder space of the barrel and the inside diameter of the container are related to each other in such a way that the stroke volume of the plunger between the position of FIG. 1 and the position of FIG. 2 is substantially equal to the volume of the container.

Figure 6:
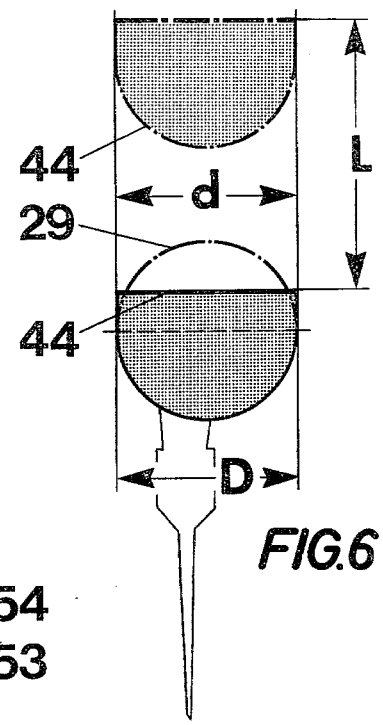
FIG. 6 is a diagram illustrating the geometrical quantities which should be related to each other for the purpose of the invention.

Referring now to FIG. 6, it is assumed that the diameter of the cylinder bore of the barrel is d, the inside diameter of the container is D, and that the stroke of the plunger from the position of FIG. 1 (empty container) to the position of FIG. 2 (filled container) is L.

The stroke volume of the plunger is determined by the relationship $$(d^2 \cdot \pi)/4 \cdot L \tag{1}$$

and the volume of the spherical container is determined by the relationship $$(D^3 \cdot \pi)/6 \tag{2}$$

In order that the flexible wall portion 35 shall closely follow the movement of the plunger head 44 during the filling operation the stroke volume of a stroke L which equals D, should be equal to the volume of the container. It follows from (1) and (2) that $$\frac{d^2 \cdot \pi \cdot D}{4} = \frac{D^3 \cdot \pi}{6} \tag{3}$$

$$d = D\sqrt{\frac{2}{3}} \tag{4}$$

$$d \simeq D \cdot 0.82 \tag{5}$$

Thus, in the preferred embodiment the inside diameter of the cylinder bore formed by the barrel should be about 82 per cent of the inside diameter of the spherical container.

In order to eject the liquid from the filled container of FIG. 2, e.g. for administering a medicament or for transferring a blood sample to a test tube, as the case may be, the container is emptied by pressing the plunger head 44 against the filled container. During this operation, needle 32 is inserted in a blood vessel or in the tissue of a human being or an animal for administering the medicament, or, alternatively, in a test tube or other receiver to which the blood sample shall be transferred for treatment or test operations.

Figure 7:
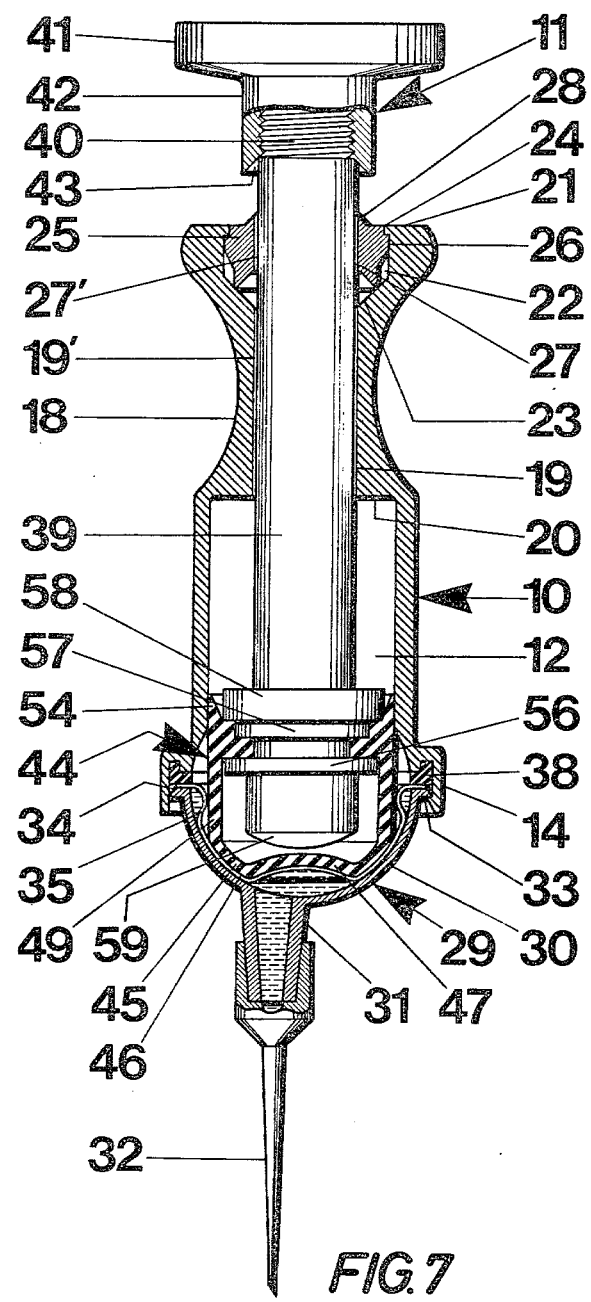
FIG. 7 is a view similar to FIG. 1 of the syringe, shown in a stage of the operation sequence when liquid is administered from the container.

During displacement of the plunger 11 axially towards container 29 from the position of FIG. 2 in which the central end wall portion 47 of the plunger head engages the spherically curved outside surface of flexible container wall portion 35, this wall portion will be introverted mechanically by the plunger head 44 and will be collapsed against the inside surface of container wall portion 30 as shown in FIG. 7. No overpressure is allowed to build up in front of the plunger head due to the fact that the portion 53 of the plunger head will allow air to pass from the front side of the piston head to the back side thereof. The valve action thus provided is an important feature of the syringe according to the invention. If air under pressure trapped between the container and the plunger head were allowed to pass into the container through a perforation in a defective container wall portion 35, the air could arrive in a blood vessel, which could be dangerous to the patient and even mortally, or a build-up of compressed air in front of the plunger head could eject the container from socket 14. If liquid leaks into cavity 12 of barrel 10 from a defective container it could be contaminated by contacting the barrel and the plunger. Such contaiminated liquid will pass to the back side of the plunger head at lip 54, where the flow resistance is lower than that in the cannula, and thus will not be administered from the syringe. This is a further safety feature of the syringe according to the teachings of the invention.

As will be seen from FIG. 7, the spherically curved surface 46 of annular end wall portion 45 of the plunger head snugly engages container wall portion 35 when introverted against container wall portion 30. The plunger head 44 in this stage of the operation has not expelled the liquid from the container completely; there is still liquid left in the container 29 centrally in front of the plunger head and also around the plunger head at the junction between container wall portions 30 and 35 where liquid will be trapped when the flexible wall portion 35 is introverted upon wall portion 30 by the plunger head 44 having a diameter which is less than the inside diameter of the container.

Figure 8:
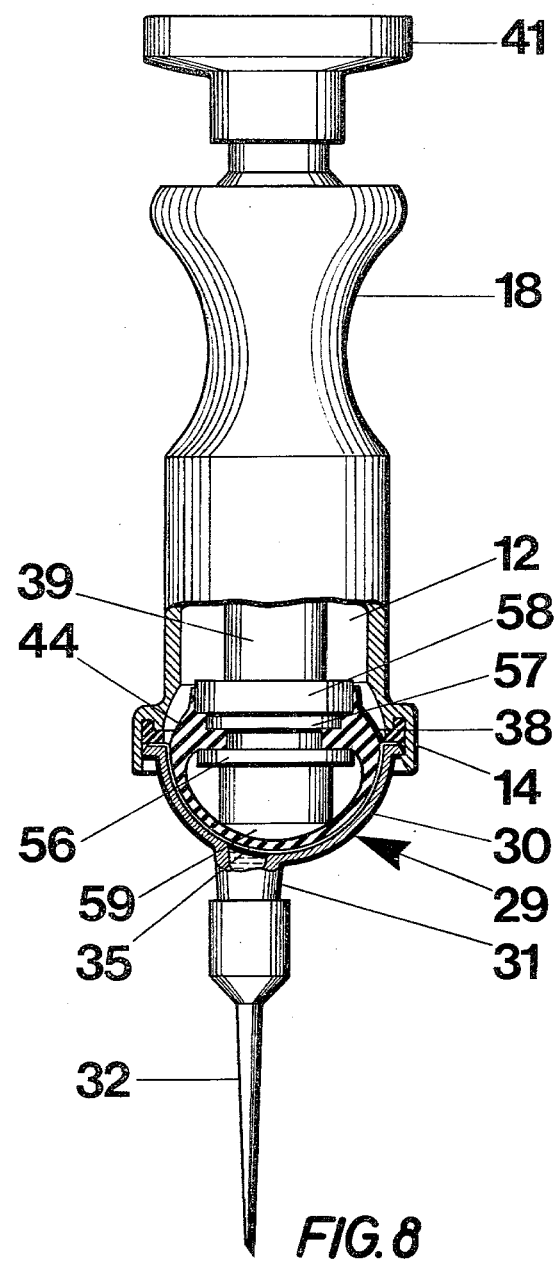
FIG. 8 is a view similar to FIG. 1 of the syringe, shown in a stage of the operation sequence wherein the liquid has been ejected from the container.
Figure 9:
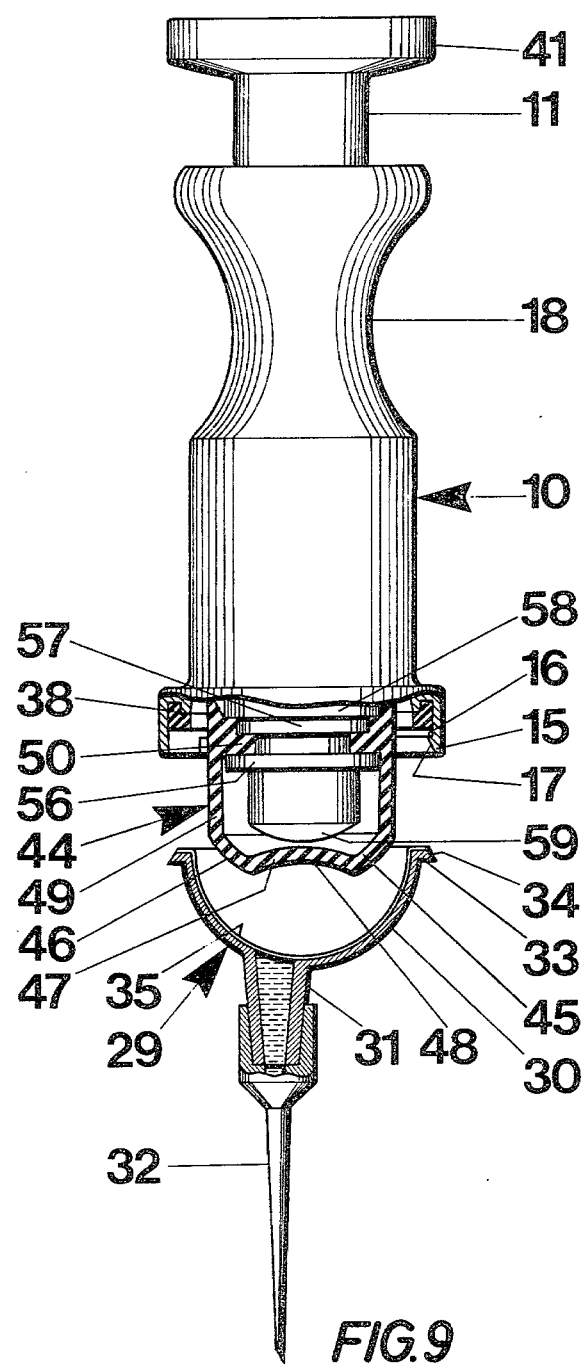
FIG. 9 is a view similar to FIG. 1 of the syringe, shown in the final stage of the operation sequence wherein the emptied container is ejected from the barrel.

In the next step of the operation of expelling the liquid from the container 29 stem 39 is further displaced axially, so that side wall portion 49 of the plunger head will be deformed so as to bulge outwards and be pressed against the introverted container wall portion 35 in the region thereof adjacent to flange 33, and the spherically curved end surface 59 of the stem will engage the inner surface of the central end wall portion 47 of the plunger head in order to deform this portion to follow the spherical form of the introverted container wall portion 35, as shown in FIG. 8. The plunger head 44 thus deformed will snugly engage wall portion 35 which is transformed to a completely introverted position wherein said wall portion follows the curvature of the inside surface of wall portion 30. Accordingly, at the end of this step there will remain no pockets between wall portions 30 and 35, the complete amount of liquid originally received by the container being expelled therefrom.

In the preferred embodiment of the plunger head 44 the spherically curved outside surface 46 of the annular end wall portion 45 of the plunger head is provided with four or more substantially radially extending tiny ribs 46′ having a height of the order of 0.1 mm. These ribs prevent portion 45 of the plunger head from completely pressing container wall portion 35 against container wall portion 30 in the operational stage shown in FIG. 7 and in the introductory part of the operational stage shown in FIG. 8 so as to allow liquid enclosed at flange 33 to pass between the container wall portions to the outlet formed by nozzle 31.

When the liquid in the container has been expelled as described above, the emptied container can be ejected from the barrel by means of the plunger. An increased force is exerted manually on the emptied container to provide a mechanical pressure thereon at the end surface 59 to deform the container to approximately the form of a truncated cone, the diameter of flange 33 being slightly reduced. Under the force thus exerted the container flange 33 is partly withdrawn from ribs 15 and finally is brought to yield so as to disengage ribs 15, FIG. 9. In this way the container can be released from the barrel together with the cannula over a waste basket and can be discarded without the necessity of manually contacting the container or the cannula which both may be contaminated by the administered liquid or by the patient. Thus, it will be seen that only a small part of the complete syringe is discarded after each use and that this can be done in a manner that avoids the risk of infection spread.

The hardness of the material from which the plunger head is made and the dimensions of the plunger head and particularly the wall thickness thereof should be chosen so that the plunger head can be deformed against the collapsed container 29 in order to expel completely the liquid therefrom in the manner described, by a force which is not sufficient for ejecting the container from the barrel. Otherwise, the container could be ejected before the operation of administering the liquid has been completed.

As an example, a plunger head 44 shaped as shown in FIG. 5, had an axial length a from flange 50 to the end of the plunger head of 9.5 mm and a diameter b at the base of the flared portion 53 of the plunger head of 13.8 mm. Portions 45, 47, and 49 of the plunger head all had a wall thickness of 1.2 mm. The plunger head was made of aged nitrile rubber having a hardness of 60° Shore.

Container 29 can also be delivered as a prefilled container, socket 31 being closed at the free end thereof. When the container has been applied to barrel 10, socket 31 is cut off at the end thereof and cannula 32 is mounted to the socket.

The liquid is expelled from the container in the manner described above, starting from the stage shown in FIG. 2.

It is possible to have containers of different sizes for co-operation with one and the same barrel so that a number of standard volumes can be chosen by choosing a container of the desired volume, although differently sized barrels may be used for containers of different sizes. Plunger head 44 can easily be replaced by another plunger head the size of which is adjusted to the container to be used with the syringe.

It will be apparent to those skilled in the art that various modifications and variations could be made in the syringe of the invention and in the container forming part thereof without departing from the scope or spirit of the invention.

I claim:

1. A syringe comprising an elongated barrel having a discharge end, a container, means for removably attaching the container to the discharge end of the barrel to form the end wall thereof, said container having a substantially rigid first wall portion at the exterior side of the end wall and forming an inside surface, and a flexible second wall portion at the interior side of the end wall and introvertible upon the inside surface of the first wall portion, a nozzle on said first wall portion for attaching a hypodermic needle thereto, and a plunger reciprocably mounted in the barrel, the stroke volume of the plunger between displaced positions thereof corresponding to the container being empty and filled, respectively, being substantially equal to the volume of the container.

2. A syringe as claimed in claim 1 wherein the container is substantially spherical and the barrel forms a substantially cylindrical cylinder space and wherein the cylinder space has an inside diameter which is less than the inside diameter of the spherical container.

3. A syringe as claimed in claim 2 wherein the ratio of the inside diameter of the spherical container and the inside diameter of the cylindrical cylinder bore is approximately $1:\sqrt{\frac{2}{3}}$.

4. A syringe as claimed in claim 1 wherein the plunger comprises a stem displaceably guided for axial movement in the barrel, said stem having an outer end outside the barrel and an inner end inside the barrel and a resilient plunger head connected to the inner end of the stem.

5. A syringe as claimed in claim 4 wherein the resilient plunger head comprises a hollow plunger head of a resilient material connected to the stem to enclose the inner end thereof, the inner surface of the plunger head being spaced from the inner end surface of the stem.

6. A syringe as claimed in claim 2 wherein the plunger comprises a stem displaceably guided for axial movement in the barrel, said stem having an outer end outside the barrel and an inner end inside the barrel, and a hollow plunger head of a resilient material connected to the stem to enclose the inner end thereof, the inner surface of the plunger head being spaced from the inner end surface of the stem, and wherein at least part of the external surface of said hollow plunger head is curved spherically.

7. A syringe as claimed in claim 6 wherein the radius of curvature of the spherically curved portion of the hollow plunger head is substantially equal to the radius of curvature of said flexible second wall portion when introverted upon the inside surface of said first wall portion.

8. A syringe as claimed in claim 6 or 7 wherein said spherically curved portion comprises an annular end wall portion of said hollow plunger head, surrounding a central end wall portion of the plunger head.

9. A syringe as claimed in claim 8 wherein said central end wall portion of the hollow plunger head is domed towards the interior of the hollow plunger head.

10. A syringe as claimed in claim 9 wherein the domed central end wall portion of the hollow plunger head forms an outside concave surface having substantially the same radius of curvature as said flexible second wall portion of the container when introverted upon the inside surface of said first wall portion of the container.

11. A syringe as claimed in claim 10 wherein said inner end surface of the plunger stem is convex.

12. A syringe as claimed in claim 11 wherein said end surface has a radius of curvature which is substantially equal to the inside radius of curvature of the central end wall portion of the hollow plunger head.

13. A syringe as claimed in claim 12 wherein the difference between the radius of curvature of said end surface and the radius of said flexible second wall portion of the container when introverted upon the inside surface of said first wall portion of the container is equal to the thickness of the central end wall portion of said hollow plunger head.

14. A syringe as claimed in claim 6 wherein said spherically curved end wall portion of the hollow plunger head joins a side wall portion surrounding the inner end portion of said stem spaced therefrom, said side wall portion being attached to the stem at a location spaced from said inner end of the stem.

15. A syringe as claimed in claim 6 wherein the hollow plunger head forms an inside annular flange and wherein said stem forms an annular groove receiving said flange for attaching the hollow plunger head to the stem.

16. A syringe as claimed in claim 6 wherein the hollow plunger head comprises an annular spherical end wall portion having an outside radius of curvature corresponding substantially to the radius of curvature of said flexible second wall portion of the container, when introverted upon the inside surface of said first wall portion of the container, a central end wall portion spherically domed towards the interior of the hollow plunger head, and a side wall portion joining the annular end wall portion, said side wall portion surrounding the stem spaced therefrom and being attached to the stem at a location spaced from said inner end thereof.

17. A syringe as claimed in claim 16 wherein said central end wall portion has an outside radius of curvature which substantially equals the radius of curvature of said flexible second wall portion of the container when introverted upon the inside surface of said first wall portion of the container, and wherein said inner end surface of the stem is convex, the difference between said radius of curvature of said second wall portion and the radius of curvature of said end surface being substantially equal to the thickness of said central wall portion.

18. A syringe as claimed in claim 6 wherein the hollow plunger head forms a conical lip on the outside thereof flared towards the end of the barrel which is opposite to the discharge end thereof, and engaging the inside wall surface of the barrel, said lip allowing air to pass between the plunger and the inside wall surface of the barrel when the plunger is being displaced towards the discharge end, and being forced to sealing engagement with said inside wall surface of the barrel when the plunger is being displaced away from the discharge end of the barrel.

19. A syringe as claimed in claims 15 and 18 wherein said flared portion projects from said flange.

20. A syringe as claimed in claim 19 wherein said flared portion terminates in a lip portion projecting inwardly towards the stem.

21. A syringe as claimed in claim 14 wherein said wall portion surrounding the stem tapers conically towards the spherically curved wall portion of the hollow plunger head.

22. A syringe as claimed in claim 1 wherein said means for removably attaching the container to the barrel comprises a circumferential flange on the container, and wherein said barrel forms a cylindrical socket at the discharge end thereof receiving said flange and forming circumferentially spaced inside projections for retaining engagement with the flange.

23. A hollow plunger head comprising a spherically curved annular end wall portion, a central end wall portion domed spherically towards the interior of the hollow plunger head, and a side wall portion joining said annular end wall portion, which tapers slightly towards said central end wall portion.

24. A hollow plunger head as claimed in claim 23 wherein said side wall portion forms an inwardly projecting flange on the inside surface thereof, spaced axially from said annular end wall portion.

25. A hollow plunger head as claimed in claim 23 wherein said side wall portion at the end thereof which is opposite to said annular end wall portion forms a conical lip on the outside thereof flared towards said end of the side wall portion.

26. A hollow plunger head as claimed in claim 25 wherein said flared portion terminates in a lip portion projecting inwardly.

* * * * *